United States Patent [19]

Glish, Jr.

[11] 4,039,843

[45] Aug. 2, 1977

[54] COMPLEMENTARY MASK IMAGE DIGITIZER METHOD AND APPARATUS

[76] Inventor: John Peter Glish, Jr., 10132 Brookside Ave., Bloomington, Minn. 55431

[21] Appl. No.: 641,261

[22] Filed: Dec. 16, 1975

[51] Int. Cl.² .................... G02B 27/38; H01J 39/12
[52] U.S. Cl. .......................... 250/550; 250/237 R; 350/162 SF
[58] Field of Search ....... 250/237 G, 237 R, 568–570, 250/550; 356/202, 203, 175; 350/162 SF

[56] References Cited

U.S. PATENT DOCUMENTS 3,836,254  9/1974  Barringer .................... 250/237 G Primary Examiner—Eli Lieberman
Assistant Examiner—David K. Moore

[57] ABSTRACT

A scanning microdensitometer comprising complementary sampling aperture components which produce positive and negative contributions to the sample measurements.

8 Claims, 3 Drawing Figures

COMPLEMENTARY MASK IMAGE DIGITIZER METHOD AND APPARATUS

BACKGROUND OF THE INVENTION

This invention describes a method and apparatus to scan and digitize images, such as photographic prints, transparencies or object produced images. Most digital image processing systems depend on the conversion of an image from its photometric density to digital values. The customary apparatus to measure these values from transparency or opaque images has been either a flying spot scanner, laser scanner or image scanning microdensitometer. These methods sweep a suitable chosen light spot over the image and detect the transmitted or reflected intensities. This detected value is a direct measure of the image density or gray level. Thus an analog-to-digital conversion of this electronic measurement provides the desired digitized value. A line-by-line scanning and detection in this manner allows digital image reproduction for applications such as image enhancement, change detection or video telecommunication.

A universal deficiency of image digitizers is the shape and intensity distribution of the scanning spot: in previous non-coherent scanning instruments, the scanning spot (or scanning aperture) has spatial frequency characteristics of degraded response below maximum frequency values of interest and non-zero response above these values. This in turn causes aliasing, excessive noise content and modulation of the desired sampled data. Previous instruments are restricted to the utilization of non-negative intensitity distributions, which is a fundamental limitation of many optical systems. With the exception of coherent scanning techniques, only limited success in removing these digitizing deficiencies has been achieved.

The elimination of aliasing and noise, as well as sharp limiting frequency cutoff can be achieved by a unique utilization of positive and negative scanning apertures as described in this invention. The shape and intensity distribution of these apertures have two generally desired configurations, however special applications will sometimes dictate other forms. This is specifically desirable for image processing in which considerable computation has previously been required to correct the sampled data. In many cases these distortions in the digitized data cannot be removed.

The application of incoherent optical techniques to achieve positive and negative components has been applied to the science of optical correlation. In this respect, relatively large area patterns are compared with the image to determine the presence of particular image patterns. The invention described herein is distinct from these area correlation instruments: area correlation instruments are specifically designed to detect the presence of image patterns irrespective of position or orientation, on a large or macro scale. This invention, conversely, provides optimized image digitizing using suitable chosen scanning spots or apertures on a microdensitometer scale. The correlation instrument measurement is a correlation value, whereas the digitizer instrument measurement is a series of density measurements.

SUMMARY OF THE INVENTION

This invention provides a method of sampling optical images with positive and negative terms of suitable selected masks to produce optimized, digitized, gray scale samples. These positive and negative components result from either temporally or spatially multiplexing the samples and separate electronic measurements. Associated with each component is a positive or negative optical mask, each having a transparency (or intensity) distribution corresponding to the positive and negative components of an optimum, matched filter of the specific digitizing system and image being scanned. For many applications, these masks are generated from the positive and negative terms of the rotationally symmetric Bessel function (first kind, order one). Subtraction of these components provides for an ideal low pass filter. That is, the sampled data has a nearly constant, rotationally-symmetric, spatial frequency response below the specified cutoff frequency. There is nearly zero frequency response above this value. These masks are complementary in that transparent (or non-zero intensity) regions of one mask correspond to opaque (or zero intensity) regions of the second mask. The desired frequency response, specific image distortions and other optical properties dictate the utilization of a variety of these complementary masks.

Three general embodiments of this invention are described, however the method clearly supports a variety of these implementations which are obvious to those skilled in the art. The first embodiment results by optically projecting the complementary masks onto the image. The image is transported in two dimensions to achieve the scanning motion. The size of the spots at the image is adjusted to correspond to the specific sample interval, however they are approximately the size of the sample interval. The complementary masks are either alternately projected or spatially separated to allow independant photodetector measurements. In the latter case, a delay line memory is required to match the subtraction of measurements from identical image cells. The detectors are appropriately located either behind transparencies or in front of photographic prints.

In a second embodiment of this invention, the photographic print or transparency is optically imaged on the complementary masks. Either a beamsplitter or a dual lens system can be used to achieve the necessary separation of positive and negative terms. The masks, located at the lens image surface, are transparencies which allow the appropriate spatial intensity distribution to impinge on the detector. (A corresponding method applies to masks constructed with photographic prints.) Scanning is accomplished by appropriately transporting the image or detection assembly, or by optically deflecting the beam.

The third embodiment is a variation of the second, however the photographic print or transparency is replaced by a real, physical object. One particular application of this instrument is an airborne or satellite based spin-scan camera.

An important property of this invention is the selection of the complementary masks. For most image digitizing applications, one of two particular types are recommended: two dimensional masks equal to or approximating the positive and negative values of the function $\sin x / x$ or the Bessel function of the first kind, order one. In addition, optimized digitizing requires that the effective size of the spot or aperture be matched with the sample interval. This is accomplished by suitable selection of mask size and lens characteristics. Variations, distortions and other image properties will dictate the use of appropriately modified masks.

DETAILED DESCRIPTION OF THE INVENTION

Figure 1:
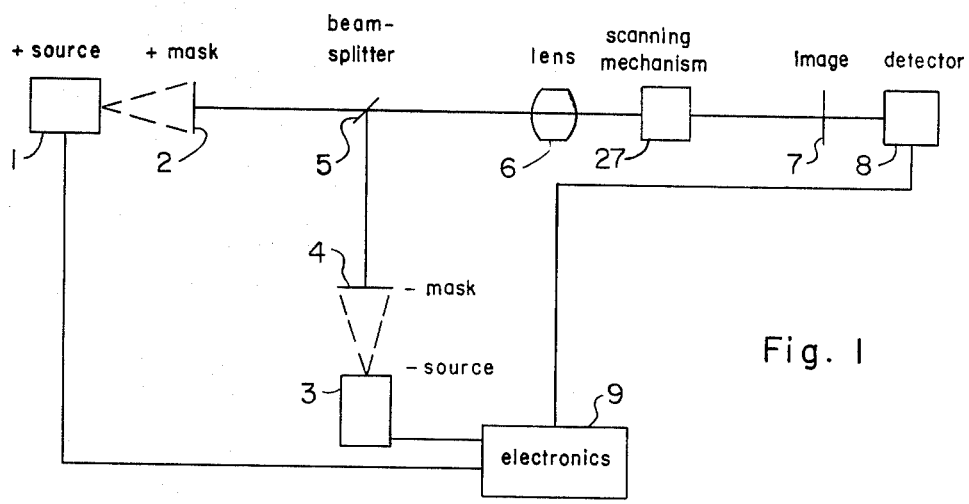
FIG. 1 illustrates an embodiment of the invention in which the complementary masks are projected onto the photographic print or transparency.

The description of this invention requires a formulation based on two dimensional sampling theory. As shown in FIG. 1, an image 7 having orthogonal coordinates denoted by $x$ and $y$ is located at the image surface of lens 6. The beamsplitter 5 permits the positive mask 2 and negative mask 4 to be alternately projected onto the image 7 by control of the illumination sources 1 and 3 from the control electronics 9. The samples are generated from measurements of the detector 8.

In the normal digitizing mode, samples are taken at regular intervals of $x$ and $y$, denoted by $x_n$ and $y_m$ respectively. The sizes of these intervals are $\Delta x_n$ and $\Delta y_m$. At each sample point the measured detector signal from the positive mask, $r_p$, is defined by $$r_p(x_n,y_m) = c_p \int \int i(x,y) \cdot q_p(x-x_n, y-y_m) \, dx \, dy,$$

where $c_p$ is a constant (determined by illumination levels and detector response), $i(x,y)$ is the image gray level and $q_p(x-x_n,y-y_m)$ is the intensity distribution of the positive mask at the image surface. In many applications $q_p(x-x_n,y-y_m)$ will be zero for $x$ and $y$ values appreciably distant from $x_n$ and $y_m$. Integration is required only over a confined area about the sample point $x_n,y_m$ in this case.

Similar results apply for the detector response of the negative mask, $r_n$. The actual sample value at each sample point is then defined by the difference $$r(x_m,y_m) = r_p - r_n.$$

This subtraction, either analog or digital, is accomplished using conventional methods within the control electronics 9.

An important property of these spatially oriented values is their corresponding frequency response which is defined by their Fourier transforms. At each sample point, the measured values ($r_p$ and $r_n$) form a convolution product. Since convolution in the spatial domain corresponds to multiplication in the frequency domain, the frequency response of the positive mask detector measurement is $$R_p = I(f_x,f_y) \cdot Q(f_x,f_y).$$

In this equation I and Q are the frequency response functions of $i(x,y)$ and $q(x,y)$. $f_x$ and $f_y$ are the frequency domain coordinates corresponding to $x$ and $y$.

The optimum sampling aperture is one having a constant frequency response from zero to some limiting frequency $f_{max}$ and zero frequency response above this value. The sample interval determines the maximum spatial frequencies that can be measured. These frequencies are $1/\{2\Delta x\}$ and $1/\{2\Delta y\}$ for the $x$ and $y$ coordinates respectively.

In some sampling systems, the desired frequency response of $Q(f_x,f_y)$ is one having rotational symmetry about each sample point. For this application the samples are usually taken such that the $x$ and $y$ sample intervals are equal and the maximum frequency response is $$f_{max} = 1/\{2\Delta x\} = 1/\{2\Delta y\}.$$

The aperture or sample mask required in the spatial domain is defined by the inverse transform of $Q(f_x,f_y)$ and is the Bessel function of the first kind, order one. The positive and negative values of the function define the distribution of the positive mask 2 and negative mask 4. These masks are complementary in that opaque regions of one correspond to regions having non-zero transparency on the other. By alternately projecting the positive and negative mask at each sample point and subtracting the two measured values, the desired sampling response is accomplished.

There are many obvious variations of the physical embodiment presented in FIG. 1. For clarity, the invention is described with a single interval and stepwise increments of the image by scanning means 27. For applications in which the image is continuously transported, for example on a rotating drum, a slight rotation of the beamsplitter is required to accurately align the positive and negative samples. In another variation, the high speed switching of the two mask projections can be eliminated by scanning the same trace twice. During the first scan, one set of measurements is stored in a memory device. During the second scan, the complementary set of measurements is taken and the subtraction can be performed. Those skilled in the art will recognize the variety of optical and mechanical implementations to achieve variable projected image sizes and sample intervals. Furthermore, the image in FIG. 1 is a transparency. This method also applies to photographic prints by adjusting the film and detector to measure reflected illumination. These results apply equally to black and white or color processing.

The intensity distribution of the complementary masks will be the Bessel function for most applications. Nevertheless, variations of these masks are clearly required for certain situations. For example, if the image moves an appreciable distance during the sample measurement, appropriate corrections of the mask distributions are required. Some applications will require a rectangular rather than rotationally symmetrical frequency response. A complementary mask distribution proportional to the function $$[\sin\{f_x x\} / \{f_x x\}] \cdot [\sin\{f_y y\} / \{f_y y\}]$$

will achieve this result. Many images have known defects such as motion blur or camera distortions. These can be removed in many cases by using suitably modified complementary masks.

Figure 2:
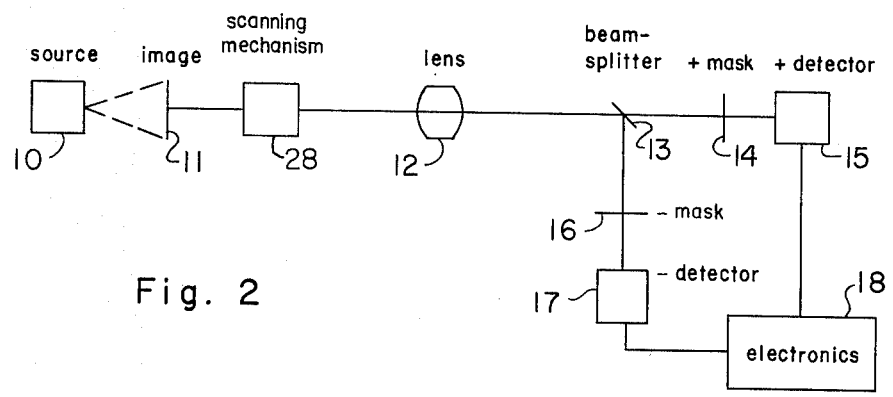
FIG. 2 illustrates an embodiment of the invention in which the photographic print or transparency is projected onto the complementary masks.

Another embodiment of this invention is presented in FIG. 2. Here an illuminated transparency 11 is projected by the lens 12 onto both the positive mask 14 and negative mask 16, which are both in the image surface of the lens 12. As in FIG. 1, the beamsplitter 13 provides for utilization of both masks and a suitable optical-mechanical means 28 provides for scanning motion. However, this embodiment does not require alternating sources of illumination and the complementary measurements can be taken simultaneously. This embodiment also lends itself to a variety of modifications which are obvious to those skilled in the art.

Figure 3:
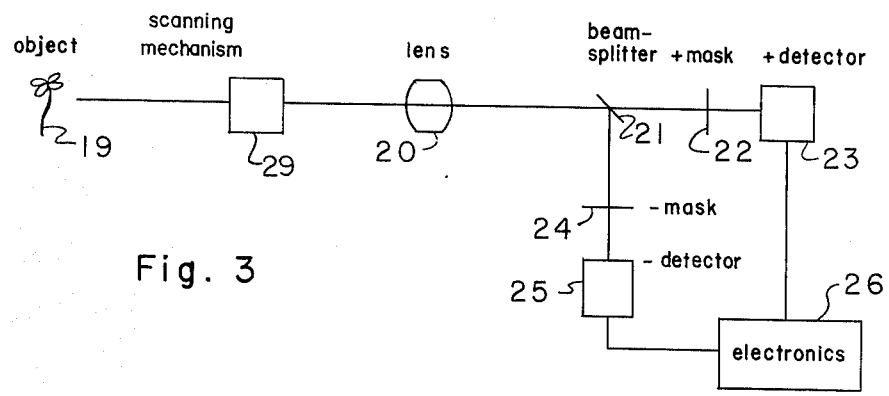
FIG. 3 illustrates an embodiment of the invention in which a real object is digitized with the complementary mask method.

A third embodiment of this invention is presented in FIG. 3. This is similar to FIG. 2, except the film (photographic print or transparency) is replaced with a real object. In FIG. 3 a suitable optical and mechanical transport is required to move the image past the masks and photodetectors. An example for air-borne applications is using the flight path for one dimension and rotation of the entire assembly for the second dimension. A second approach is to combine the optical and mechanical scanning means 29. For example, an aircraft flight path provides one dimension and a rotating mirror in front of the lens 20 would provide the second scanning dimension. A third approach is to create the entire scanning motion within the instrument by appropriate optical and mechanical means.

What is claimed is:

1. A method of sampling an image such as a photographic print, transparency or object produced image consisting in:
    a. Selecting complementary masks each having an appropriate transform domain response determined by specific image properties and desired sampling function response, wherein one mask has an intensity distribution of positive components required in sampling aperture and is elswhere opaque, and the other mask has an intensity distribution corresponding to negative components required in sampling aperture and is elswhere opaque,
    b. Projecting mask patterns onto image sample point or projecting image sample point through said masks,
    c. Separately measuring illumination of combined mask/image sample point response as effected by each of said complementary masks.
    d. Combining complementary measurements to produce optimized spatial image sample as determined at each image sample point $(x_n, y_m)$ by the desired sampling response $$c \int \int i(x,y) \, q(x-x_n, y-y_m) \, dx \, dy$$

where $c$ is a constant determined by ambient conditions, $i(x,y)$ represents image intensity variations and $q(x-x_n, y-y_m)$ represents positive and negative variations of the sample aperture produced by complementary masks, and e. Indexing over image sample points and repeating steps (b) through (d) to produce optimized samples of entire image.

2. A method of sampling images in accordance with claim 1, wherein the spatial frequency spectrum of the sampled image has an approximately constant response up to an arbitrarily selected threshold frequency and an approximately zero response above said threshold frequency.

3. A method of sampling images in accordance with claim 2, wherein aliasing, noise and modulated frequency response are removed from the sampled data, and complementary masks are appropriately selected for image properties and desired sample spectrum.

4. An apparatus to produce discrete samples of an image, such as a photographic print, transparency or object produced image comprising:
    a. Complementary mask means having intensity distributions with appropriate transform domain characteristics to produce positive and negative sample apertures at each sample point, which effect optimized image samples as determined at each saple point $(x_n, y_m)$ by the desired sampling response $$c \int \int (x,y) \, q(x-x_n, y-y_m) \, dx \, dy$$

where $c$ is a constant determined by ambient conditions, $i(x,y)$ represents image intensity variations of $q(x-x_n, y-y_m)$ represents positive and negative variations of the sample aperture produced by comlementary masks,
    b. Optical means to project and control image sampling apertures,
    c. Means to optically or mechanically scan the image,
    d. Detector means to measure intensities of complementary sample components, and
    e. Electronic means to control operation and sequencing of said masks, image optics, scanning and detection means, said electronic means being operable to subtract and digitizemeasurements to produce optimized, discrete image samples having desired response function characteristics.

5. An apparatus in accordance with claim 4, wherein complementary spots are projected onto a transparency and intensities transmitted thru said transparency are sampled.

6. An apparatus in accordance with claim 4, wherein complementary spots are projected onto a photographic print and reflected intensities are sampled.

7. An apparatus in accordance with claim 4, wherein an image from a photographic print or transparency is projected onto complementary masks and intensities transmitted thru or intensities reflected from complementary masks are sampled and digitized.

8. An apparatus in accordance with claim 7, wherein an image from a real object is sampled and digitized.

* * * * *